United States Patent
Lee et al.

(10) Patent No.: US 7,155,366 B2
(45) Date of Patent: Dec. 26, 2006

(54) APPARATUS AND METHOD FOR INSPECTING PATTERNS ON WAFERS

(75) Inventors: Chang-Hoon Lee, Cheonan-si (KR); Byung-Am Lee, Suwon-si (KR); Byung-Seol Ahn, Suwon-si (KR); Jae-Sun Cho, Suwon-si (KR); Joo-Woo Kim, Seoul (KR); Sung-Man Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 64 days.

(21) Appl. No.: 10/999,066

(22) Filed: Nov. 30, 2004

(65) Prior Publication Data

US 2005/0119844 A1    Jun. 2, 2005

(30) Foreign Application Priority Data

Dec. 1, 2003    (KR) ............................ 2003-86368

(51) Int. Cl.
G06F 3/00    (2006.01)

(52) U.S. Cl. ................. 702/182; 702/179; 702/183; 702/185

(58) Field of Classification Search ............ 702/83, 702/179, 181–183, 189, 185; 382/149; 700/110; 706/16
See application file for complete search history.

(56) References Cited

U.S. PATENT DOCUMENTS 5,131,755 A * 7/1992 Chadwick et al. .......... 356/394
6,483,938 B1 * 11/2002 Hennessey et al. ......... 382/149
6,961,085 B1 * 11/2005 Sasaki .................... 348/222.1

FOREIGN PATENT DOCUMENTS

| JP | 2002-267615 | 9/2002 |
|---|---|---|
| JP | 2003-101948 | 4/2003 |
| KR | 1997-0077405 | 12/1997 |
| KR | 2000-0016881 | 3/2000 |

* cited by examiner

*Primary Examiner*—Marc S. Hoff
*Assistant Examiner*—Felix Suarez
(74) *Attorney, Agent, or Firm*—Volentine Francos & Whitt, PLLC

(57) ABSTRACT

A wafer pattern inspecting apparatus and method are disclosed. The apparatus comprises an image sensor to acquire image data from a reference die and a sample die, an external memory to store the image data, an encoder to compress the data, a decoder to decompress the data, an internal memory device to store the compressed image data of the reference die, an arithmetic module to process the image data for the reference dies to extract a reference image data, a reference storage memory to store compressed reference image data, and a comparison module to compare the sample die image data with the reference image data to an extract defect data for the sample die.

22 Claims, 9 Drawing Sheets

APPARATUS AND METHOD FOR INSPECTING PATTERNS ON WAFERS

BACKGROUND OF THE INVENTION

1. Field of the Invention

The present invention generally relates to an apparatus and a method for inspecting patterns formed on a wafer. More particularly, the present invention generally relates to an apparatus and a method for inspecting dies on a semiconductor wafer to determine the position of pattern defects.

A claim of priority is made to Korean Patent Application No. 2003-86368, filed on Dec. 1, 2003 in the Korean Intellectual Property Office, the disclosure of which is incorporated herein in its entirety by reference.

2. Description of the Related Art

A conventional semiconductor wafer includes a plurality of dies where integrated circuit devices are printed thereon. The integrated circuit device is fabricated by complex processes, including a series of inspection steps performed on patterns formed on the integrated circuit device. A complete inspection is typically performed to verify the accuracy of the patterns formed on the wafer. One conventional inspection method is a die-to-die method. The die-to-die method is a method where a sample die is compared with its adjacent dies.

The conventional die-to-die method will now be described with reference to FIG. 1.

As shown in FIG. 1, a conventional wafer has a plurality of two-dimensionally partitioned dies. In the die-to-die method, a sample die 1 is inspected by comparing the patterns formed on die 1 with the patterns formed on adjacent dies 2 and 3.

In the case where a die 4 is disposed at an edge of a wafer, adjacent dies 5 and die 6 are selected as reference dies, because there is only one immediate adjacent die 5. Here, die 4 is a non-functional die, because it is an incomplete die. If a pattern at a specific position on sample die 4 is identical to at least one of reference dies 5, 6, that position is determined as defect-free, i.e., normal.

In another scenario, if a similar defect occurs at the same position on both reference dies, the sample die will be deemed defective even if that position on the sample die is normal. Furthermore, in the case where the sample die and one of the reference dies are similarly defective at the same position, the pattern corresponding to this position on the sample die will be deemed normal. As described above, die 4 disposed at the wafer edge is non-functional. When die 5 is inspected, because die 4 is incomplete and non-functional, and if die 6 is defective, die 5 will be deemed as defective even though it is normal.

The die-to-die method is inaccurate; therefore, a better inspection method is required.

SUMMARY OF THE INVENTION

In one aspect, the present invention provides an apparatus and a method for inspecting patterns on a die and accurately determining pattern defects on the die.

In another aspect, the present invention provides an apparatus and method for accurately inspecting patterns on a sample die without reference to adjacent dies.

In still another aspect, the present invention provides a pattern inspecting apparatus for extracting a reference value to accurately determine a defect in a sample die, and a pattern inspecting method for inspecting defects in sample dies using the reference value.

In order to achieve these aspects, the present invention provides an apparatus for inspecting die patterns on a wafer having an image sensor to acquire image data from a reference die and a sample die, an external memory to store the image data acquired by the image sensor, an encoder to compress the image data, a decoder to decompress a compressed image data, an internal memory device to store compressed image data for the reference die, an arithmetic module to process the reference die image data to extract a reference image data, a reference storage to store the compressed reference image data, and a comparison module to compare the image data from the sample die with the reference image data to extract pattern defect data for the sample die.

The present invention also provides a method for inspecting die patterns formed on a wafer by sampling a plurality of reference dies, acquiring image data from the plurality of reference dies, compressing the acquired image data, dividing the respective compressed image data for each one of the plurality of reference dies into a plurality of blocks, and processing the compressed image data for the respective blocks to extract reference data, acquiring image data from a sample die, and comparing the image data from the sample die with the reference image data to extract defect data for the sample die.

DETAILED DESCRIPTION OF THE INVENTION

The present invention will now be described more fully with reference to the accompanying drawings, in which preferred embodiments of the invention are shown. The invention may, however, be embodied in different forms and should not be construed as limited to the embodiments set forth herein. Rather, these embodiments are provided as teaching examples of the invention. Like numbers refer to like elements throughout the specification.

Figure 1:
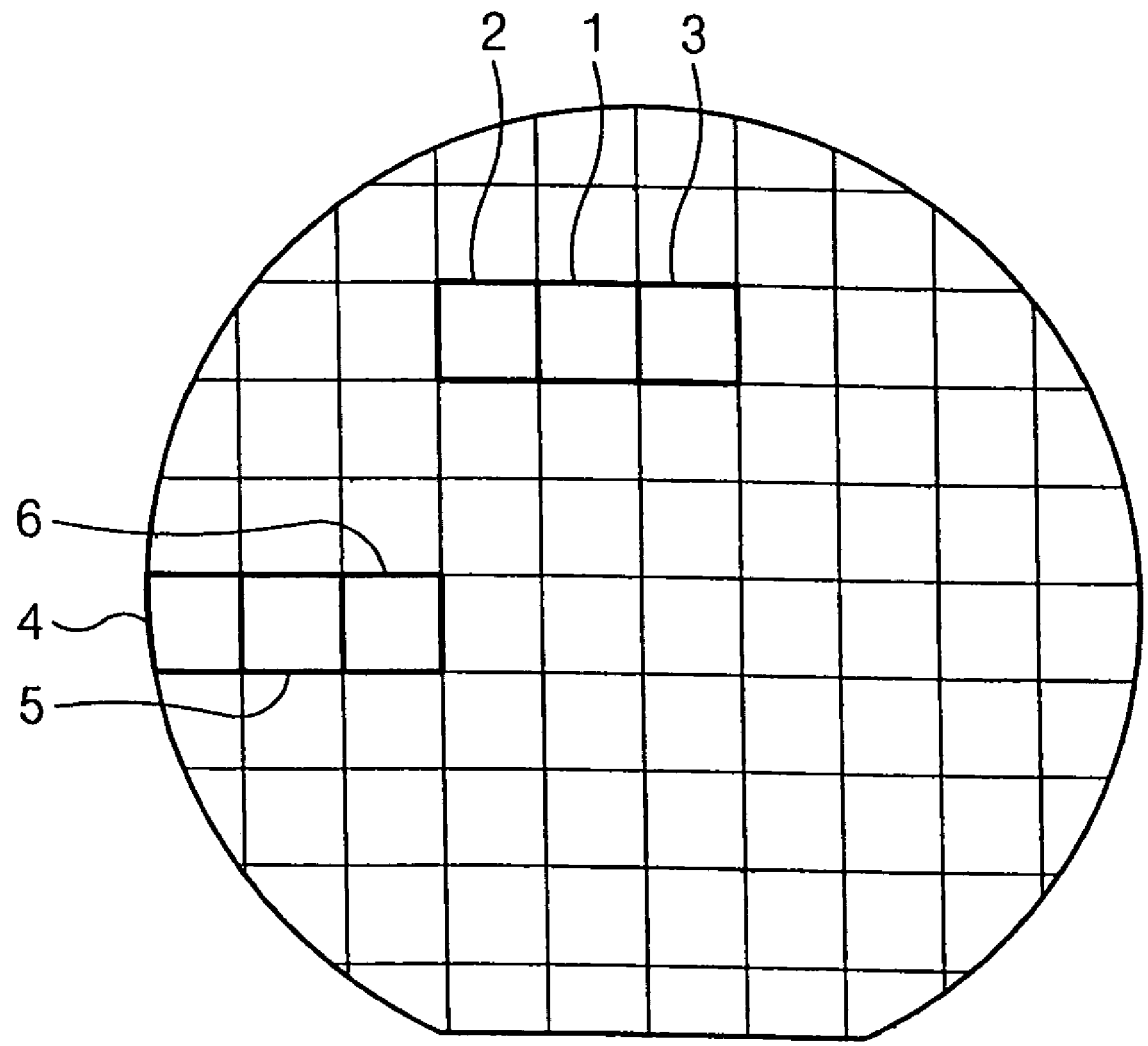
FIG. 1 is a top plan view of a wafer to explain the conventional die-to-die method.
Figure 2:
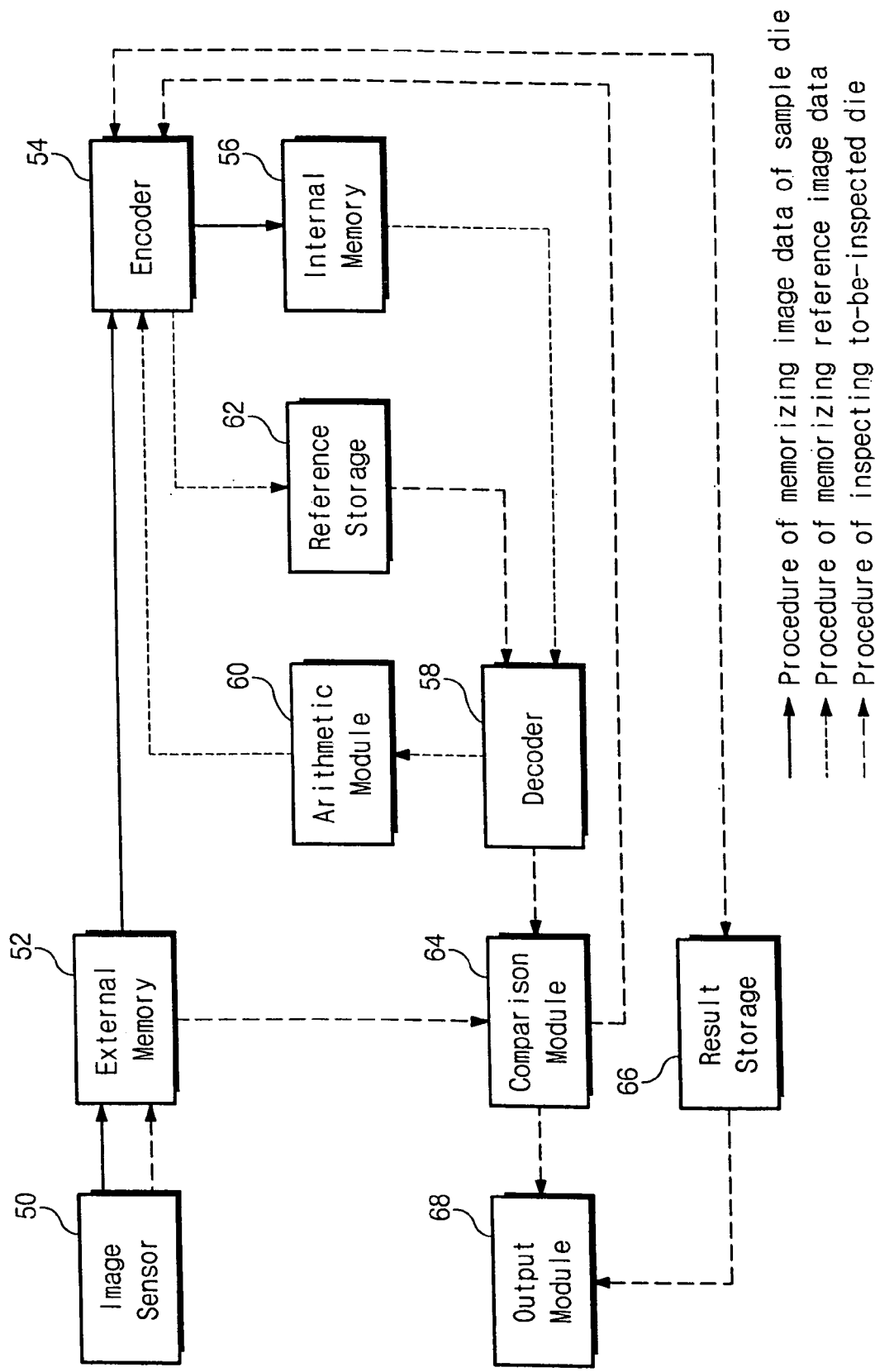
FIG. 2 is a block diagram of a pattern inspecting apparatus according to a preferred embodiment of the present invention.

FIG. 2 is a block diagram of a pattern inspecting apparatus according to a preferred embodiment of the present invention. Referring to FIG. 2, the pattern inspecting apparatus includes: an image sensor 50 to acquire image information from a die on a wafer; an external memory 52 to store the acquired image information (data); an encoder 54 to compress the image data; a decoder 58 to decompress the compressed image data; a reference storage 62 to store reference image data; and, a comparison module 64 to compare sample die image data with the reference image data. The pattern inspecting apparatus further comprises an internal memory 56 and an arithmetic module 60 activated during a procedure to extract reference image information from a plurality of sample dies. Arithmetic module 60 and comparison module 64 are preferably embedded in the same data processing unit. The pattern inspecting apparatus may further comprise an output module 68 to output detected defect data, and a result storage memory 66 to store the detected defect data.

In further detail, image sensor 50 acquires image data from a die, typically including an array of two-dimensional pixels. Each of the pixels corresponds to position data on the die and to image data for that position. The smaller the size of the pixel, the more accurately a pattern can be inspected. For example, as pixel size decreases in proportion to a minimum pitch size for the sample integrated circuit device; the ability to accurately acquire an image data is inversely proportional to the pixel size. Thus, as pixel size decreases, the resulting quantity of the image data increases. The volume of the image data also increases with segmentation of measurement values for the image data as well as the pixel size. As the measurement values of the respective pixels are segmented, the ability to measure micro defects is enhanced. In order to accurately detect micro defects, it is preferable to reduce the pixel size and to segment the measurement values for the image data, even where the resulting volume of image data increases accordingly.

Image sensor 50 sequentially acquires image data in the form of a two-dimensional array of pixels. The acquired data is transmitted and stored in external memory 52. External memory 52 acts as a buffer to temporarily store the acquired image data. Preferably, external memory 52 has sufficient storage capacity to store all image data acquired from all sampled dies. However, with the recent trend toward smaller patterns, it may be difficult to process the entire volume of image data acquired from a plurality of dies. Therefore, in the present invention, the acquired data is optionally compressed in order to reduce the volume of data requiring storage and processing.

Image sensor 50 preferably acquires image data from a reference die and a sample die. A reference image data setting procedure is preferably divided into an image data memory procedure for the reference die and a reference image data memory procedure. In the image data memory procedure related to the reference dies, image sensor 50 acquires image data from at least one sample reference die. If a plurality of sample reference dies are selected according to their positions on the wafer, image sensor 50 acquires the image data from the sample reference dies and transmits the acquired data to external memory 52. The image data for one or more sample reference dies is preferably acquired and transmitted depending on the volume of image data for the die and the capacity of external memory 52. The sample reference die image data stored in external memory 52 is divided into a plurality of blocks and compressed for each respective block, and then eventually transmitted to internal memory 56. Each of the blocks includes data related to the two-dimensionally array of pixels and corresponding block position data. The sample reference die image data for the respective block is transmitted to encoder 54. Encoder 54 compresses the image data and transmits the compressed block data to internal memory 56. If the capacity of external memory 52 is insufficient, the block data transmitted to encoder 54 may be erased from external memory 52 after a period of time. If the block data transmitted to internal memory 56 is reconfigured according to the corresponding position data to transmit a final compressed block data. In this manner, compressed image data for the sample reference die is completely stored. By repeating the above procedure, image data for the sample reference die is compressed and stored in internal memory 56.

After storing image data for the reference dies is complete, the reference image data storing procedure preferably begins. However, the reference image data storing procedure may alternatively start at the time when first block data of compressed image data from the final sample reference die is transmitted to internal memory 56. In the reference image data storing procedure, image data from the sample reference dies stored in internal memory 56 are restored for each block to be processed by arithmetic module 60. The block data having the same corresponding position data as the respective sample reference die is selected for transmission to decoder 58. Arithmetic module 60 performs a series of processing procedures on the restored block data to extract reference block data. The reference block data is compressed at encoder 54 and sequentially stored in reference storage 62. When the reference data for the last block is transmitted to reference storage 62, the reconfiguration of the reference image data is complete.

In the procedure to inspect a sample die, i.e., a to-be-inspected die, image sensor 50 acquires image data for the sample die. The acquired image data is transmitted to external memory 52. Comparison module 64 compares the image data for the sample die with the reference image data at the respective block in order to detect a defect. The respective block reference image data stored in reference storage 62 is restored, and then transmitted to comparison module 64. Also, the respective block image data for the sample die, which is stored in external memory 52, is transmitted to comparison module 64. In this case, the blocks to be compared have the same position data. The defect data detected by comparison module 64 is transmitted to output module 68, and then output or stored in result storage memory 66. The defect data may be compressed at encoder 54, and then stored in result storage memory 66. Result storage memory 66 preferably stores the defect data for each wafer and thereby forms a wafer defect map.

A pattern inspecting method according to a preferred embodiment of the present invention will now be described with reference to the flowchart shown in FIG. 3.

Figure 3:
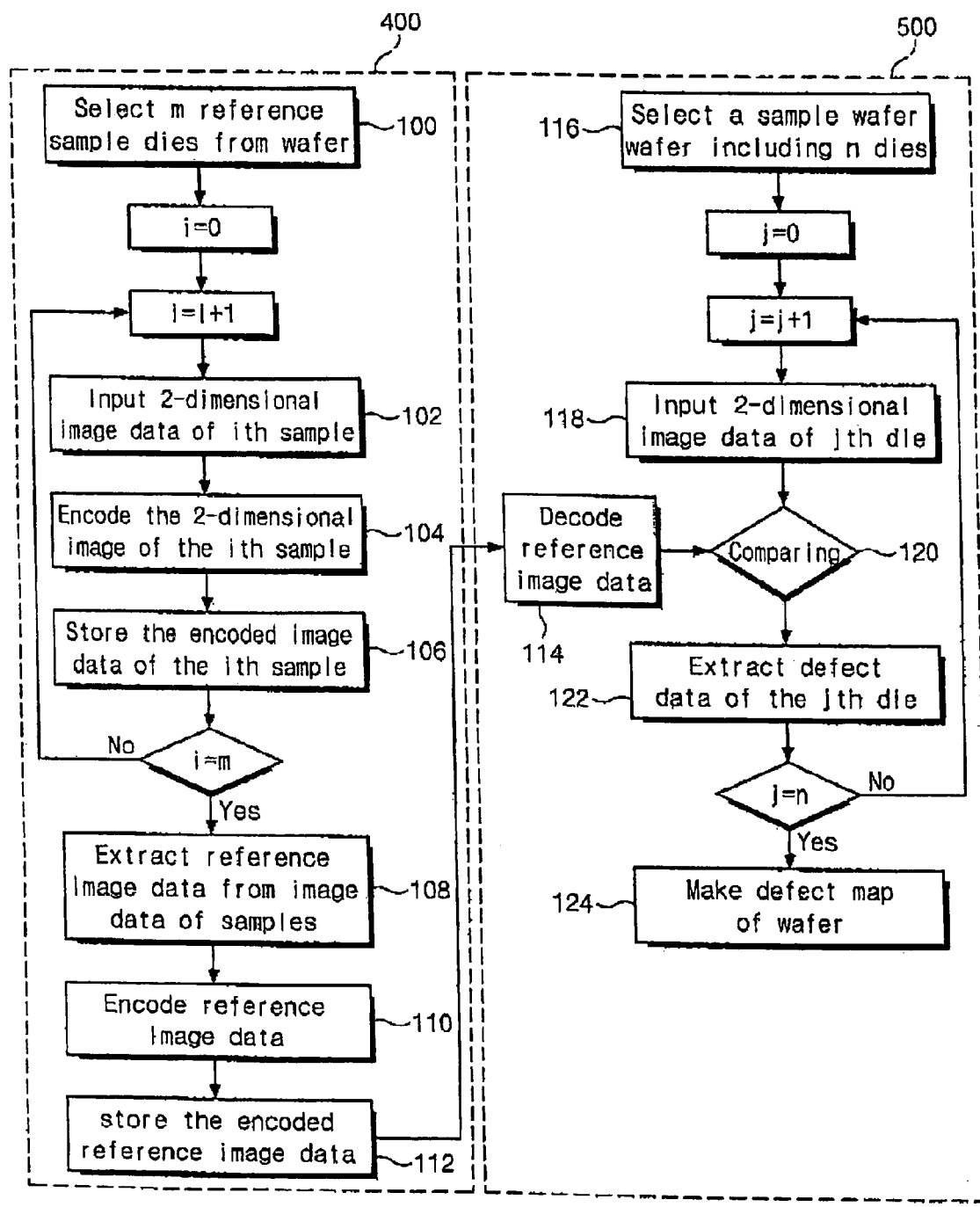
FIG. 3 is a flowchart for explaining a pattern inspecting method according to a preferred embodiment of the present invention.

Referring to FIG. 3, the pattern inspecting method includes reference image data setting steps 400 and die inspecting steps 500. Steps 400 begin with a sample die selecting step 100 and ends with an encoded reference image data storing step 112. Steps 500 begin with a sample wafer selecting step including n dies 116 and ends with defect mapping step 124. The step of selecting a sample wafer 116 and step of decoding reference image data 114 are independently performed.

Steps 400 will now be described hereinafter. On a wafer, "m" reference sample dies are selected (100). An identification (i) is assigned to each of the sample dies. A two-dimensional image data for the first sample is input (102). The two-dimensional image data is preferably acquired by image sensor 50, and stored in external memory 52. The two-dimensional image data is encoded (104). The encoded image data is stored (106). Steps 102–106 are carried out for all of the reference sample dies. The ID of current reference sample die is checked to determine whether the data input for all of the reference samples is complete. When the data input for all reference samples is stored, a reference image data is extracted from the samples (108). The extracted reference image data is encoded (110). The encoded reference image data is stored (112), and the reference image data setting steps (400) are complete. The larger the number of reference sample dies, the better the reference image data. However since the number of reference samples are proportional to the execution time for the image data setting steps, the number of reference samples are preferably selected within a permissible value.

The die inspecting steps 500 begin when a sample wafer is selected (116). The sample wafer may be identical to the reference sample wafer in selected step 100. Independently of steps 500, the encoded reference image data is decoded (114). The sample wafer preferably has "n" sample dies. Identification (j) is assigned to each of the sample dies. Image data forth first die sample is input (118). The input image data for the first sample die is compared with the reference image data (120). Defects are determined based on the comparison between the first die sample and the reference image data (122). Based on the comparison, defect data of the first die sample is extracted (122). The ID of a sample die is checked, and steps 118–122 are repeated until the ID equals the vlaue n. When defect data for the n sample dies is extracted, a defect map for the sample wafer is constructed (124).

Figure 4:
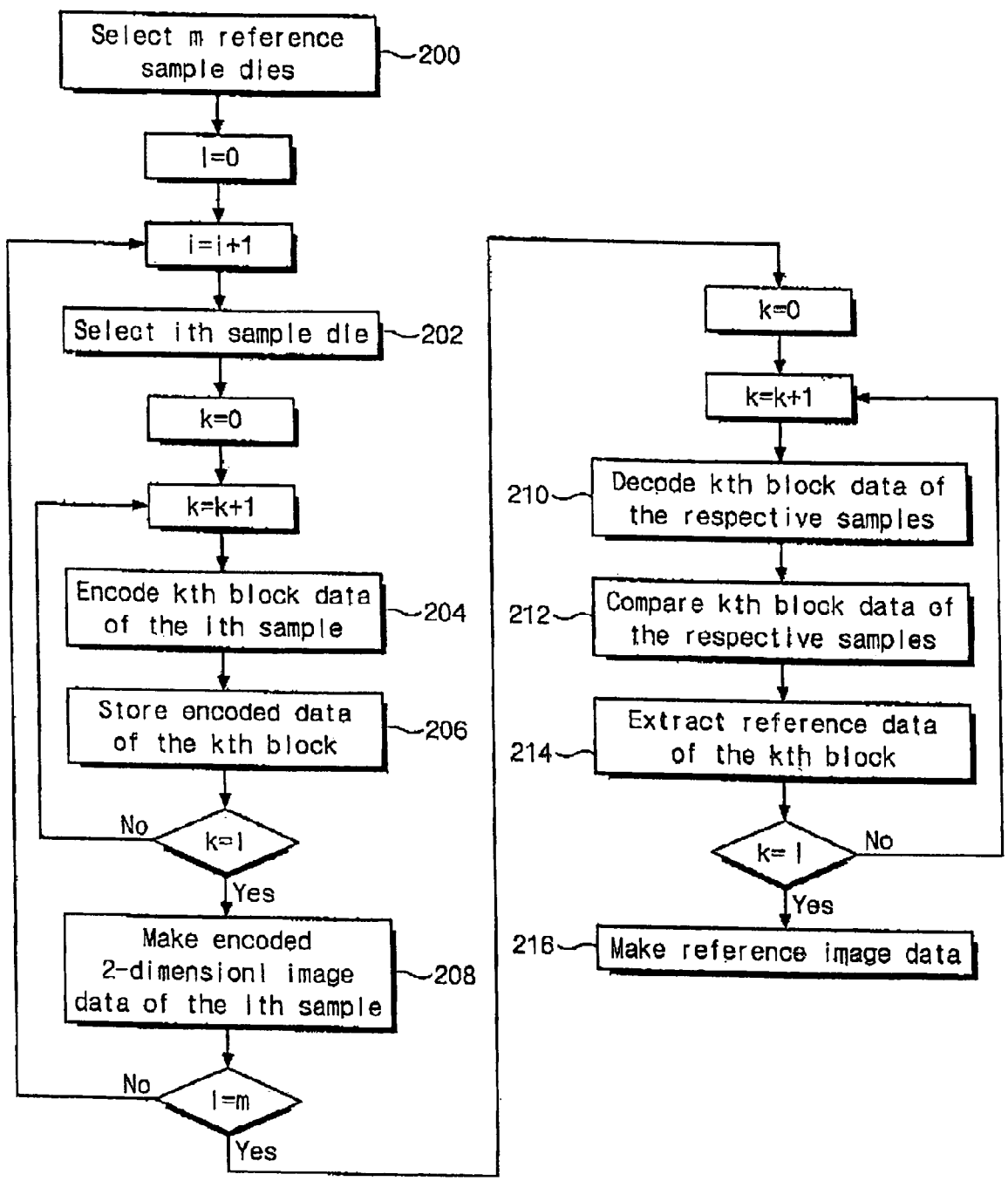
FIG. 4 is a flowchart showing steps of setting a reference image data in the pattern inspecting method according to the preferred embodiment of the present invention.

FIG. 4 is a flowchart further illustrating the reference image data setting steps according to a preferred embodiment of the present invention. First, "m" reference sample dies are selected (200). The number of selected reference sample dies is preferably selected in consideration of the accuracy and processing time for the resulting reference data. For example, three reference sample dies are selected. An identification (i) is assigned to each of the reference sample dies. A first reference sample is selected (202). Each of the reference sample dies is preferably divided into "l" blocks. An identification (k) is assigned to each of the blocks. A first block data is encoded in a block unit (204), and then the encoded block data are stored (206). Each of the blocks includes corresponding position data for the reference sample die. When the encoded data for an entire block of the first reference sample die is stored, the ID of the reference sample die is checked, and steps 202–208 are performed on the next sample. After the completion of step 208, the ID of the reference sample die is checked. If the checked ID equals the value m, the block ID (k) is initialized and the first block data for each reference sample is decoded (210). The first block data for the reference sample dies, i.e., m first block data sets are compared (212), and reference data for a first block is extracted from the first block data (214). All of the blocks are sequentially decoded, and the decoded blocks are compared (210–214). When the reference data for the respective blocks has been extracted, the ID of the block is checked. If the ID equals the value "l", the extraction of reference data is complete. The extracted reference position data is arranged to configure the reference image data (216).

Figure 5:
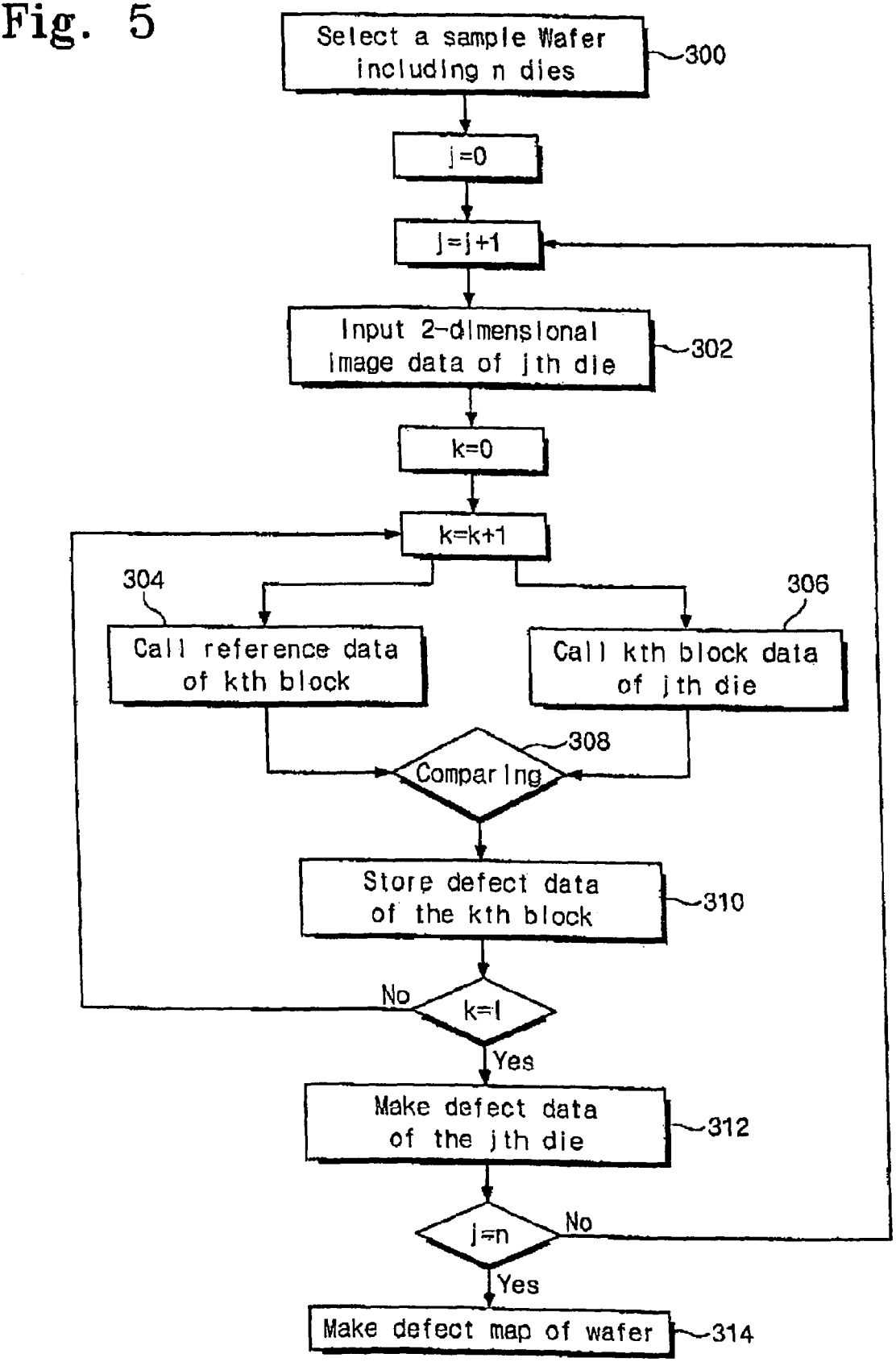
FIG. 5 is a flowchart showing steps of inspecting a sample die in the pattern inspecting method according to the preferred embodiment of the present invention.

The die inspecting steps according to the preferred embodiment of the present invention will now be described with reference to the flowchart shown in FIG. 5. First, a sample wafer is selected (300). The wafer has "n" sample dies. An identification (j) is assigned to each of the sample dies. Two-dimensional image data for the first die is input (302). A die is divided into "l" block. An identification (k) is assigned to each of the l blocks. Reference data for a first block and the first block data for the sample die are retrieved (304 and 306). The reference data is compared with the sample die block data to determine any defects in the first block (308). The first defect data is stored (310), and the block ID is checked. Steps 304–310 are repeated until the block ID equals the value "l." The defect data for the first sample die is configured from the defect data extracted when the block ID is "l" (312). The defect data is preferably output by an output module. To acquire the defect data for the entire wafer, this routine proceeds to the next die and steps 302–312 are repeated until the ID of the current die equal the value "n". When the ID of the die reaches "n", the extraction of defect data from the n sample dies is complete. According to the entire die position, a defect data is used to make a defect map for the wafer (314).

Figure 6:
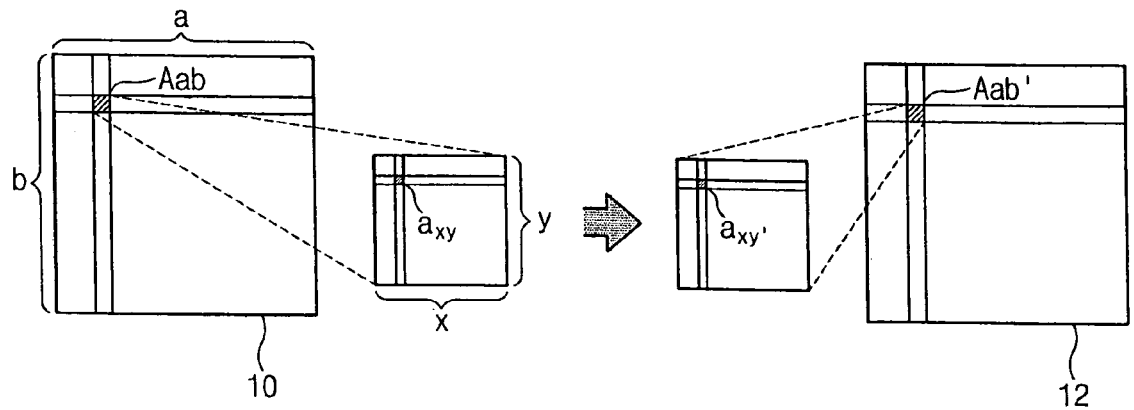
FIG. 6 through FIG. 8 shows compression of image data of a sample die according to the preferred embodiment of the present invention.
Figure 7:
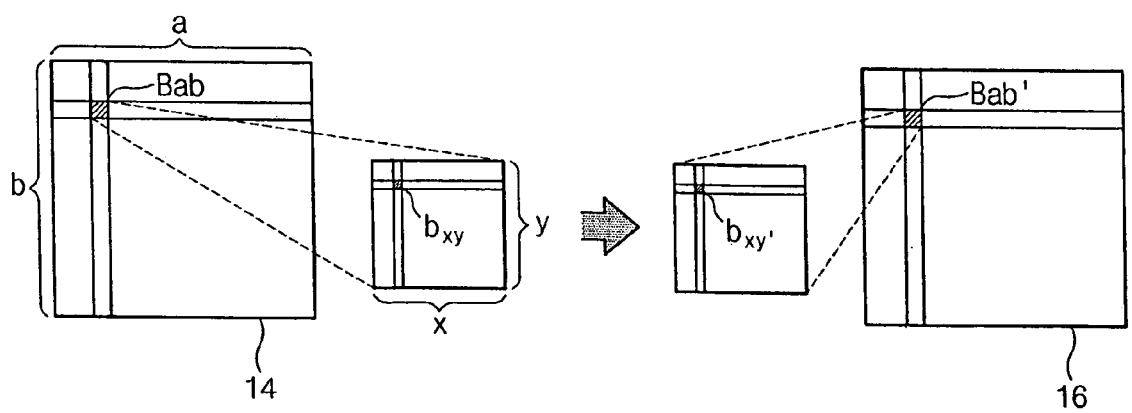
Figure 8:
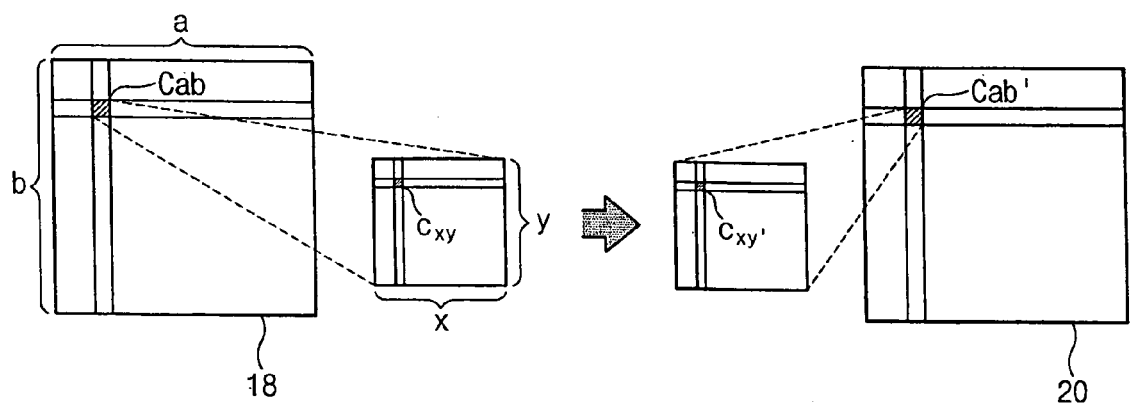

FIG. 6 through FIG. 8 illustrate compression of image data for a sample die. Referring to FIG. 6, compression of the image data is performed by an encoder. Image data for a sample die is composed of two-dimensional array of pixels and a two-dimensional image data for the sample die. Image data 10 for a first sample die is divided into axb block ($A_{ab}$). Each block has corresponding position data for each image. Each block is composed of xxy pixels ($a_{xy}$) each having image data and position data. Block data temporarily stored in an external memory is sequentially selected to be transmitted to the encoder. The encoder compresses the selected block data in order to encode it. The compressed image data is restored by the lossless image compression method, where the higher the number of repeated patterns on a die, the better the compressibility of the data. As a result, compressed block data $A_{ab}'$ is reduced in size and composed of changed pixels $a_{xy}'$. The compressed block data $A_{ab}'$ has position data for each pixel and position data for the block. Thus, compressed image data 12 for the sample die is acquired by reconfiguring the compressed block data $A_{ab}'$.

Referring to FIG. 7, after compressing the image data for the first sample die is complete, compression of an image data for a second sample die begins. The image data for the second sample die is composed of axb block ($B_{ab}$), and each of the block is composed of xxy pixels ($a_{xy}$). Similar to the compression of the first image data, compressed block data $B_{ab}'$ having changed pixel data is acquired by compressing the data for the respective blocks. The compressed block data $B_{ab}'$ is reconfigured to acquire a compressed image data 16 for the second sample die.

Referring to FIG. 8, compressed image data $C_{ab}'$ for a third sample die is acquired in the same manner as described above. Image data 18 for the third sample die is composed of axb block ($C_{ab}$), each having xxy pixels ($c_{ab}$). A compressed image data 20 is composed of block $C_{ab}'$ having changed pixels $c_{ab}'$.

The number of samples is determined in consideration of the processing speed and accuracy of the reference image data. The size of a sample die, the size of a block, and the size of a pixel are preferably identical throughout all the sample dies. Each pixel and block have corresponding position data. The compressed image data has the original position data, and its capacity is reduced. Thus the compressed image data is decoded to restore the original image data, and decoding is conducted by a lossless compression method to restore the original image data.

Figure 9:
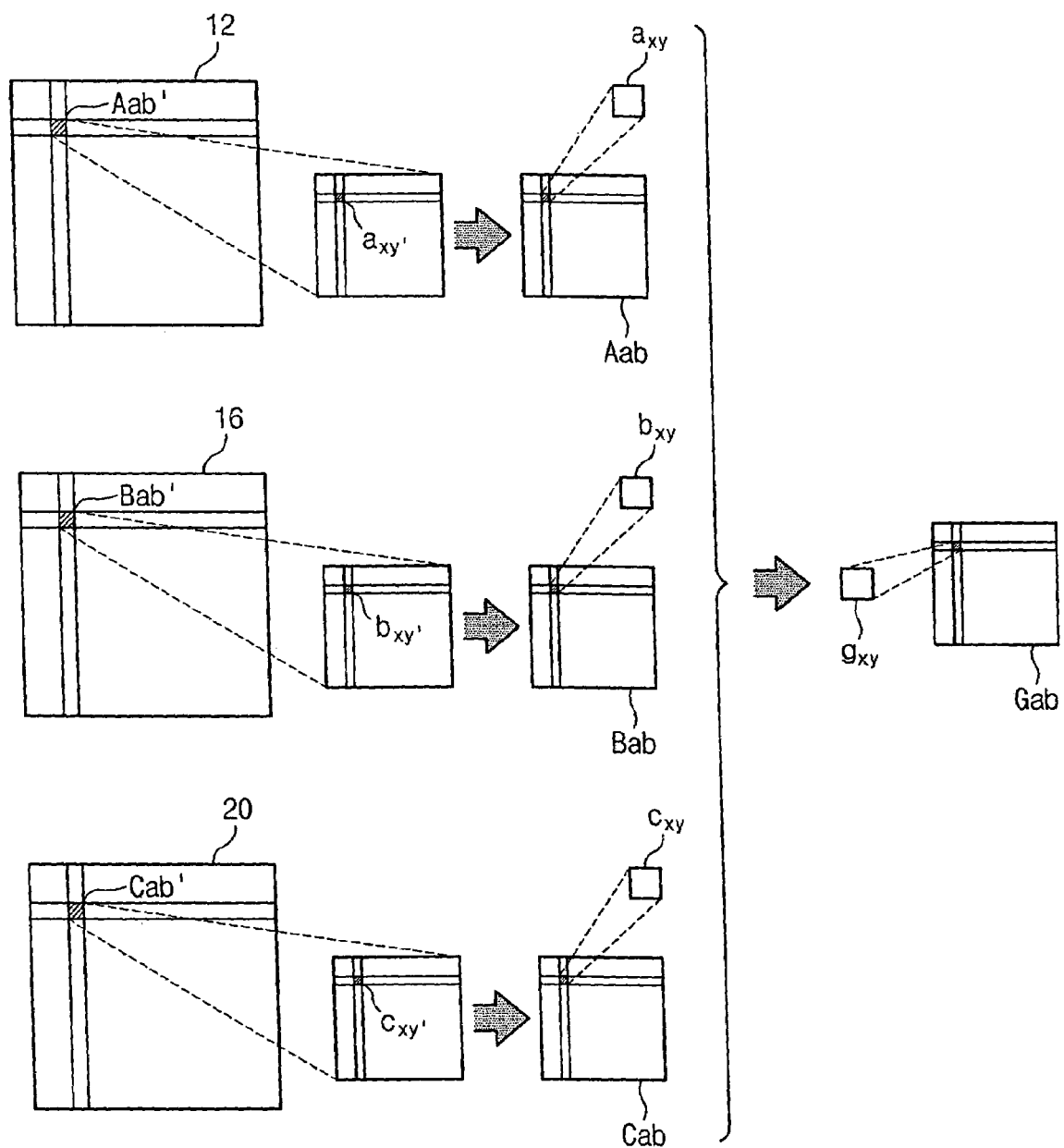
FIG. 9 and FIG. 10 show a method for extracting reference image data from compressed image data of the sample die according to the preferred embodiment of the present invention.

A method of extracting reference image data from compressed image data for a sample die will be described with reference to FIG. 9 and FIG. 10. Referring to FIG. 9, a reference image data is extracted for each respective block. The compressed block data $A_{ab}'$, $B_{ab}'$, and $C_{ab}'$ are selected from the compressed image data 12, 16, 20 for the respective sample dies. The selected block data $A_{ab}'$, $B_{ab}'$, and $C_{ab}'$ have the same position data. The compressed block data $A_{ab}'$, $B_{ab}'$, and $C_{ab}'$ are restored. The decoder may decode the compressed block data $A_{ab}'$, $B_{ab}'$, and $C_{ab}'$. The restored block data $A_{ab}$, $B_{ab}$, and $C_{ab}$ are processed to extract reference block data $G_{ab}$. Specifically, pixels $a_{xy}$, $b_{xy}$, and $c_{xy}$ having the same position are selected one by one from the respective block data $A_{ab}$, $B_{ab}$, and $C_{ab}$, and image data corresponding to the pixel is processed to define a reference value. In this case, a median of the pixel image data is defined as a reference value. For example, in the case where the image data is related to an intensity of light and its values are 50, 75, and 90 respectively, the reference value is 75. All pixels are sequentially compared to acquire block data $G_{ab}$ having reference values $g_{xy}$ corresponding to pixels $g_{xy}$. This procedure may be performed by the arithmetic module.

Figure 10:
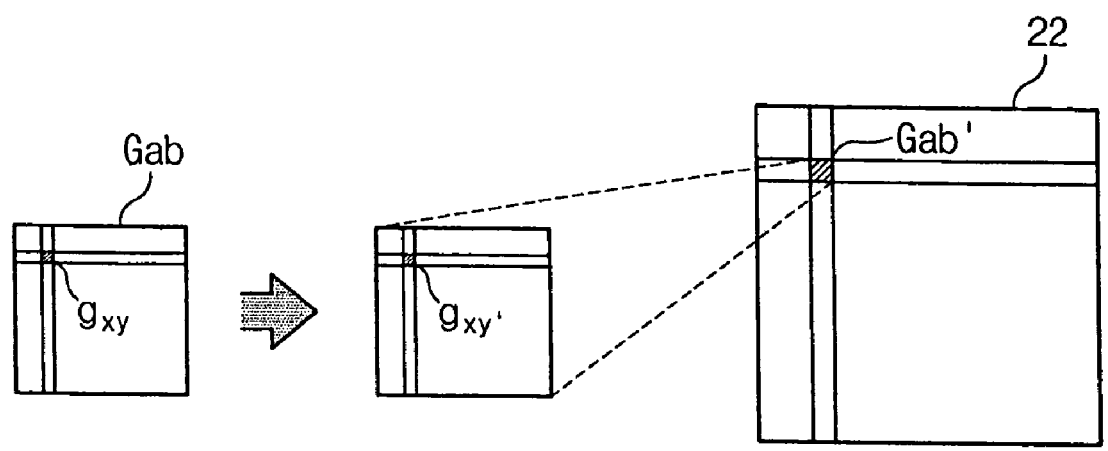

Referring to FIG. 10, in the arithmetic module, reference block data $G_{ab}$ is transmitted to a reference storage memory. Specifically, reference block data $G_{ab}$ acquired at each respective block is compressed into a compressed block data $G_{ab}'$. Then compressed block data $G_{ab}'$ is stored in the reference storage memory. The block data is memorized according its position data. Simultaneously with the storage of the block data, reference image data 22 may be configured.

Figure 11:
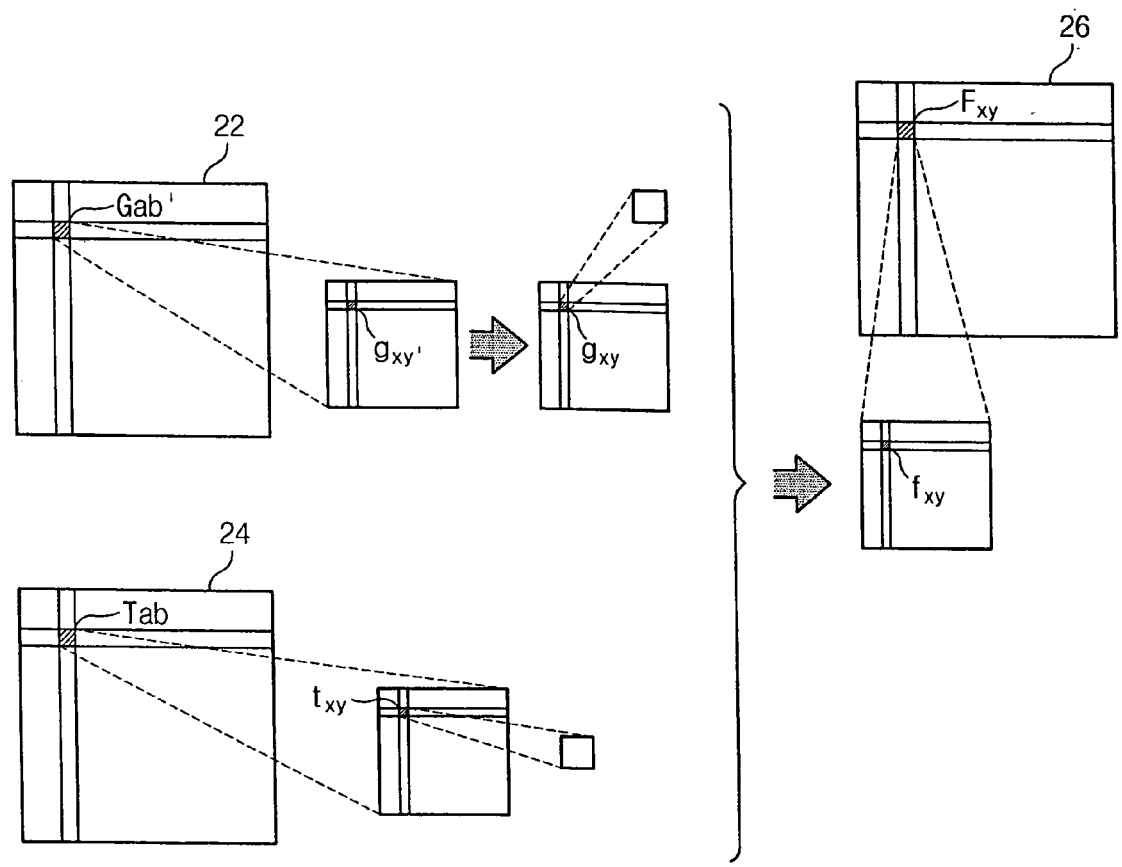
FIG. 11 shows steps of inspecting a sample die according to a preferred embodiment of the present invention.

FIG. 11 shows the steps of inspecting a sample die according to a preferred embodiment of the present invention. Referring to FIG. 11, reference image data 22 extracted from the same wafer as the sample die is selected. Reference image data 22 may be extracted in advance. An image data 24 of the sample die is acquired. Block data $G_{ab}$ is selected block-by-block from reference image data 22 and image data 24. The reference image data $G_{ab}$ is stored while being compressed. Therefore, block data $G_{ab}'$ selected from reference image data 22 is restored at a decoder. A reference pixel (value) $g_{xy}$ for restored block data $G_{ab}$ and a block data $T_{ab}$ of the sample die are compared with each other one at a time. The one pixels are compared by a comparison module that offers a threshold value to the image data of reference pixel $g_{xy}$ to determine whether it is defect-free or not. When the image data of a sample pixel $t_{xy}$ is within the threshold value, it is determined to be defect-free. When the image data of the sample pixel $t_{xy}$ is below or beyond the threshold value, it is determined to be defective. This procedure is sequentially performed for all pixels to configure a defect block data $F_{ab}$. Thus each pixel $f_{xy}$ of defect block data $F_{ab}$ has defect information, not image information. The entire block of image data 24 of the sample die are compared with reference image data 22 to acquire defect data 26 for the sample die. This result is output by an output module. In this case, the output results may be distinguished by a user. A defect position and a defect aspect for the sample die may be inspected at the same time by overlapping image data 24 and defect data 26. The defect data is stored in a result storage memory. Alternatively, the defect data is compressed at a decoder for storage or is stored as a defect map for the wafer by reconfiguring the sample dies.

As disclosed, reference image data is extracted from a plurality of selected reference sample dies. By comparing the reference image data with a sample, defects in the sample die can be precisely determined. Further when a wafer having successive defects is inspected, errors caused by adjacent dies can be prevented. Since image data for a sample die is compressed, the amount of data processing can be reduced. In addition, the image data is processed by respective blocks to extract reference image data and defect data. Therefore, it is possible to achieve real-time inspection, storage, and transmission.

While the present invention has been described in detail with reference to certain preferred embodiments, it should be apparent that modifications and adaptations to those embodiments might occur to a person skilled in the art without departing from the scope of the present invention.

What is claimed is:

1. An apparatus for inspecting die patterns on a wafer, comprising:
    a reference memory to store compressed reference image data associated with a reference die, wherein the compressed reference image data is acquired using an image sensor sampling the reference die and subsequently compressed using an image encoder;
    a decoder and an arithmetic module configured to respectively decompress and extract portions of the stored compressed reference image data to produce one or more first reference images of a die; and
    a comparison module to compare the one or more first reference images with a sample image of a die associated with the sample die to extract pattern defect data for the sample die.

2. The apparatus of claim 1, wherein each one of the encoder, decoder, arithmetic module, and comparison module divide image data into a plurality of two-dimensional image blocks, and process the image data in relation to the two-dimensional image blocks.

3. The apparatus of claim 1, wherein the image sensor converts the image of the sample die to image data defined by a two-dimensional array of pixels.

4. The apparatus of claim 1, wherein the reference memory stores compressed image data for a plurality of reference dies.

5. The apparatus of claim 2, wherein the arithmetic module is configured to extract a reference image block having the same spatial coordinates as a selected sample image block.

6. The apparatus of claim 2, wherein the comparison module is configured to compare a reference image block having the same spatial coordinates as a selected sample image block to extract defect data for the sample die relating to the selected block.

7. The apparatus of claim 6, further comprising a result storage memory to store defect data, and an output module for outputting the defect data.

8. The apparatus of claim 7, wherein the result storage memory stores defect data compressed by the encoder.

9. The apparatus as recited in claim 7, wherein the output module directly outputs the defect data, or outputs a result stored in the result storage memory.

10. The apparatus as recited in claim 7, wherein the result storage memory stores defect data compressed by the encoder, and the output module outputs the defect data stored in the result storage memory, wherein the defect data is restored at the decoder to be transmitted by the output module.

11. The apparatus as recited in claim 7, wherein the result storage memory stores a wafer defect map composed of the defect data.

12. The apparatus as recited in claim 11, wherein the output module outputs the wafer defect map stored in the result storage memory.

13. A method for inspecting die patterns formed on a wafer, comprising:
    sampling a plurality of reference dies;

acquiring image data from the plurality of reference dies, compressing the acquired image data;

dividing the respective compressed image data into a plurality of blocks, processing the compressed image data block by block to extract reference image data;

acquiring image data from a sample die; and comparing the sample die image data with the reference image data to extract defect data for the sample die.

14. The method of claim 13, wherein the sample die is selected from the same wafer as the plurality of reference dies.

15. The method of claim 13, wherein the image data is composed of a plurality of two-dimensionally pixel arrays, and wherein the image data further comprises position data and corresponding image data.

16. The method of claim 13, wherein the image data and the reference image data are each divided into a plurality of blocks and compared block by block to extract the defect data.

17. The method of claim 13, wherein compressing the acquired image data further comprises:

acquiring image data for a selected reference die; and dividing the image data for the selected reference die into a plurality of blocks and compressing the image data for the selected reference die block by block.

18. The method of claim 13, wherein the extracting the reference image data further comprises:

dividing the respective compressed image data for the reference dies into "n" blocks;

selecting an $n^{th}$ block of the respective compressed image data;

restoring the selected $n^{th}$ block;

processing the restored $n^{th}$ block to extract reference data from the $n^{th}$ block; and reconfiguring the reference data for the $n^{th}$ block to define the reference image data.

19. The method as recited in claim 18, wherein each of the blocks comprises a two-dimensionally array of "m" pixels, wherein processing the $n^{th}$ block comprises:

selecting an $m^{th}$ pixel from each of the respective $n^{th}$ blocks;

comparing image data for each of $m^{th}$ pixel from each of the respective $n^{th}$ blocks;

selecting a median value for the n selected $m^{th}$ pixels to be defined a $m^{th}$ reference pixel; and defining the reference data for the n blocks in relation to the selected median values.

20. The method of claim 13, wherein the extracting the defect data comprises:

dividing the reference image data and the sample die image data into "n" blocks;

selecting an nth block from the reference image data and the sample die image data;

comparing the selected nth blocks to extract defect data for the $n^{th}$ block; and, extracting the defect data from the "n" blocks to configure defect data for the sample die.

21. The method of claim 20, wherein the reference image data and the sample dies image data are composed of two-dimensionally pixel arrays comprising image data and position data, wherein each of the n blocks is composed of two-dimensional array of "m" pixels, and wherein extracting the defect data from the n blocks comprises:

selecting the $m^{th}$ pixel from a respective $n^{th}$ block of the reference image data and the sample die image data; comparing the image information of the $m^{th}$ pixels to determine a defect; and extracting the defect data for the $n^{th}$ block in relation to the compared $m^{th}$ pixels.

22. The method of claim 21, wherein extracting the defect comprises:

setting a threshold value for pixel image data for the reference image data; and comparing sample die image data to the threshold value.

* * * * *